United States Patent
Clifton-Climas et al.

(10) Patent No.: US 12,061,301 B2
(45) Date of Patent: Aug. 13, 2024

(54) MONITORING SYSTEM COMPRISING A PLURALITY OF PORTABLE DEVICES AND A CONTROL UNIT

(71) Applicants: SOLETANCHE FREYSSINET S.A.S., Rueil-Malmaison (FR); ISYmap, Bagnols sur Cèze (FR)

(72) Inventors: Dan Clifton-Climas, Rueil-Malmaison (FR); Adrian Davis-Johnston, Rueil-Malmaison (FR); Dominique Rothan, Rueil-Malmaison (FR); Marie-Anne Lissandre, Bagnols sur Cèze (FR); Aurélien Ballier, Bagnols sur Cèze (FR)

( * ) Notice: Subject to any disclaimer, the term of this patent is extended or adjusted under 35 U.S.C. 154(b) by 795 days.

(21) Appl. No.: 17/266,879

(22) PCT Filed: Aug. 9, 2019

(86) PCT No.: PCT/EP2019/071492
§ 371 (c)(1),
(2) Date: Feb. 8, 2021

(87) PCT Pub. No.: WO2020/030808
PCT Pub. Date: Feb. 13, 2020

(65) Prior Publication Data
US 2021/0290081 A1    Sep. 23, 2021

(30) Foreign Application Priority Data
Aug. 9, 2018  (GB) ........................................ 1812994

(51) Int. Cl.
*G01T 7/00*    (2006.01)
*G01T 1/02*    (2006.01)
(Continued)

(52) U.S. Cl.
CPC .................. *G01T 7/00* (2013.01); *G01T 1/02* (2013.01); *G01T 1/178* (2013.01); *A61B 5/0002* (2013.01);
(Continued)

(58) Field of Classification Search
CPC .............. G01T 1/02; G01T 1/178; G01T 7/00
See application file for complete search history.

(56) References Cited

U.S. PATENT DOCUMENTS

| 2003/0040869 A1* | 2/2003 | Nir ...................... H04W 56/006 |
| | | 455/502 |
| 2007/0192159 A1* | 8/2007 | Root ...................... G01W 1/00 |
| | | 705/7.34 |

(Continued)

FOREIGN PATENT DOCUMENTS

| EP | 3220369 A1 | 9/2017 |
| KR | 101207898 B1 | 2/2013 |

(Continued)

OTHER PUBLICATIONS

International Search Report (Form PCT/ISA/210) for International Application No. PCT/EP2019/071492 mailed Nov. 5, 2019, 4 pages.

(Continued)

*Primary Examiner* — Chih-Cheng Kao
(74) *Attorney, Agent, or Firm* — Withrow + Terranova, PLLC; Vincent K. Gustafson

(57) ABSTRACT

A system for monitoring the exposure of a plurality of individuals to a physical or chemical property associated with an environment. The system includes a plurality of portable devices. Each portable device is arranged to be worn or carried by an individual in the environment. The system further includes a control unit for communicating with each of the plurality of portable devices. Each portable (Continued)

device includes a detector arranged to measure a physical or chemical property that the individual wearing or carrying the device is exposed to in the environment; one or more physiological sensors each arranged to measure a physiological parameter of the individual; a geolocation module arranged to determine the location of the individual; and a communication module for communicating data collected by the portable device with other(s) of the plurality of the portable devices and with the control unit.

19 Claims, 11 Drawing Sheets

(51) Int. Cl.
| | |
|---|---|
| *G01T 1/178* | (2006.01) |
| *A61B 5/00* | (2006.01) |
| *A61B 5/0205* | (2006.01) |
| *A61B 5/024* | (2006.01) |
| *A61B 5/11* | (2006.01) |
| *G01S 5/10* | (2006.01) |
| *G01S 19/01* | (2010.01) |
| *G01T 1/36* | (2006.01) |

(52) U.S. Cl.
CPC .......... *A61B 5/02055* (2013.01); *A61B 5/024* (2013.01); *A61B 5/1112* (2013.01); *A61B 5/6801* (2013.01); *A61B 2560/0242* (2013.01); *G01S 5/10* (2013.01); *G01S 19/01* (2013.01); *G01T 1/36* (2013.01)

(56) References Cited

U.S. PATENT DOCUMENTS

| | | | |
|---|---|---|---|
| 2008/0146892 A1* | 6/2008 | LeBoeuf | A61B 5/4812 600/300 |
| 2011/0066398 A1* | 3/2011 | Troxler | G01N 23/00 702/150 |
| 2011/0105862 A1* | 5/2011 | Gies | A61B 5/1126 600/301 |
| 2011/0161111 A1 | 6/2011 | Dicks et al. | |
| 2017/0293035 A1 | 10/2017 | Badyal et al. | |

FOREIGN PATENT DOCUMENTS

| | | |
|---|---|---|
| WO | 2015160830 A1 | 10/2015 |
| WO | 2018068130 A1 | 4/2018 |

OTHER PUBLICATIONS

Written Opinion (Form PCT/ISA/237) for International Application No. PCT/EP2019/071492 mailed Nov. 5, 2019, 6 pages.

Search Report under Section 17(5) for United Kingdom Patent Application No. GB1812994.0 mailed Feb. 12, 2019, 4 pages.

Extended European Search Report for European Patent Application No. 23194317.6, mailed Dec. 4, 2023, 6 pages.

* cited by examiner

MONITORING SYSTEM COMPRISING A PLURALITY OF PORTABLE DEVICES AND A CONTROL UNIT

This application is a 35 U.S.C. § 371 national phase filing of International Application No. PCT/EP2019/071492 filed on Aug. 9, 2019, and claims the benefit of United Kingdom Patent Application No. 1812994.0 filed on Aug. 9, 2018, wherein the disclosures of the foregoing applications are hereby incorporated by reference herein in their respective entireties.

This invention relates to a monitoring system, in particular to a system for monitoring the exposure of one or more individuals to a physical or chemical property associated with an environment.

In hazardous environments that contain potentially harmful substances (e.g. radioactive materials), it is important to have an accurate measurement of the exposure an individual working in the environment has to the substance. Electronic personal dosimeters are used to monitor the exposure workers (such as radiographers and nuclear power plant workers) have to ionising radiation. This helps to ensure that a worker is not exposed to a harmful cumulative dose of radiation.

While such dosimeters are able to provide alarm warnings to their users (e.g. when the radiation dose to which they have been exposed reaches a certain level), the dosimeters are limited in their functionality.

The present invention aims to provide an improved monitoring system for individuals working in a potentially dangerous environment.

When viewed from a first aspect the invention provides a system for monitoring the exposure of a plurality of individuals to a physical or chemical property associated with an environment, the system comprising:
   a plurality of portable devices, wherein each portable device is arranged to be worn or carried by an individual in the environment; and
   a control unit for communicating with each of the plurality of portable devices;
   wherein each portable device comprises:
      a detector arranged to measure a physical or chemical property that the individual wearing or carrying the device is exposed to in the environment;
      one or more physiological sensors each arranged to measure a physiological parameter of the individual;
      a geolocation module arranged to determine the location of the individual; and
      a communication module for communicating data collected by the portable device with other(s) of the plurality of the portable devices and with the control unit.

When viewed from a second aspect the invention provides a method of monitoring the exposure of a plurality of individuals to a physical or chemical property associated with an environment, the method comprising:
   a plurality of individuals each wearing or carrying a portable device in an environment;
   a detector of each device measuring a physical or chemical property that the individual wearing or carrying the device is exposed to in the environment;
   one or more physiological sensors of each device each measuring a physiological parameter of the individual;
   a geolocation module of each device determining the location of the individual;
   communicating data collected by the plurality of portable devices between portable devices and to a control unit.

The present invention relates to a monitoring system that monitors and a method of monitoring the exposure of individuals to a chemical or physical property that may be present in an environment, e.g. in which the individuals are working. The system includes a control unit in communication with portable devices that are worn or carried by the individuals when they are in the environment.

The portable devices each include a detector for measuring a physical or chemical property associated with the environment, to which the individual wearing or carrying the device may be exposed. The portable devices also include physiological sensor(s) which monitor physiological parameter(s) of the respective individuals and a geolocation module to determine the respective locations of the portable devices (and thus the individuals). These allow physiological parameters and the locations in the environment of the individuals wearing or carrying the portable devices to be monitored, along with their exposure to the physical or chemical property.

A communication module in each portable device allows the devices in the system to communicate data collected by the devices with each other and with the control unit. This, for example, may allow the portable devices to transmit data collected by the detectors, the physiological sensors and/or the geolocation modules (e.g. in real time) to the control unit, e.g. for analysis.

Thus it will be appreciated that by augmenting the portable devices (which measure the exposure of the respective individuals to a physical or chemical property associated with the environment in which the individuals are present) with one or more physiological sensors, a geolocation module and a communication module provides the portable devices with additional functionality that is not present in conventional devices. In particular, in addition to monitoring the exposure of the individual to a physical or chemical property, the physiological sensor(s) enable the individuals wearing or carrying the portable devices to be monitored, giving additional data on the health of the individuals in what may be a harsh environment.

The geolocation module in the portable devices enables the positions of the individuals in the environment to be tracked and may, for example, allow the exposure of the individuals to the physical or chemical property and/or the measured physiological parameter(s) of the individuals to be matched (and, e.g., correlated) to their location in the environment. This may also allow the spatial dependence of the physical or chemical property to be analysed.

The communication module in the portable devices enables the captured data to be transferred to the control unit, e.g. in real time, thus allowing a full picture of the individuals' exposure to the physical or chemical property and their physiological parameter(s) to be monitored. It will be appreciated that owing to each portable device including a communication module (which may be in data communication with other(s) of the portable devices and/or the control unit), the captured data from a portable device may still be transferred back to the control unit, even when the portable device is not in direct data communication with the control unit, e.g. by transferring the data via one or more intermediately positioned portable devices.

The environment in which the individuals are present (e.g. working) and which has associated with it a physical or chemical property, may be any suitable and desired environment. The environment may, for example, be a chemical processing plant. In a preferred embodiment the environment comprises a nuclear facility, e.g. a nuclear power plant.

The environment may be inside, outside or part inside and part outside. As will be seen below, different techniques and/or hardware may be used to determine the location of the portable devices (and thus the individuals wearing or carrying them), depending on whether the environment is inside or outside.

The portable devices may be provided in any suitable and desired way that enables a portable device to be worn or carried by an individual. The components of the portable devices, including the detector, the physiological sensor, the geolocation module, the communication module and any other components discussed below, may be integrated together into a single, integral device. In other embodiments one or more of the different components of the portable device are provided separately from each other, e.g. depending on their function. For example, the detector of a portable device may need to be provided on the exterior of an individual to be able to measure the exposure of the individual to the chemical or physical property, while the physiological sensor(s) may need to be provided next to the skin of an individual to monitor the necessary physiological parameter (e.g. temperature and/or heart rate).

Whether the components of the portable devices are provided together in an integral device or separately as discrete components, preferably each of the components of a portable device are connected (e.g. via a wired or wireless connection) to the communication module. This then allows all the data captured by a portable device to be communicated back to the control unit.

For example, when the components of the portable device are provided as discrete components, the various discrete components of the portable device may comprise respective connectivity ports, transmitters and receivers, as appropriate. This allows the components of the portable device to communicate with each other, such as a plurality of physiological sensors or detectors which are not integral to the body of the portable device to communicate with the control unit. For example, this may allow a heart rate monitor attached to the chest of an individual, separate from a portable device worn on the wrist, to communicate with each other. The (e.g. discrete components of the) portable device may comprise one or more of the following ports and/or serial protocols for wired and/or wireless communication: Bluetooth Low Energy (BLE), universal serial bus (USB), serial peripheral interface (SPI), I²C, universal asynchronous receiver-transmitter (UART), general purpose input-output (GPIO), mobile industry processor interface (MIPI).

The detector of each portable device worn or carried by an individual is arranged to measure a (e.g. localised) physical or chemical property that the individual is exposed to while the individual is wearing or carrying the portable device in the environment. Preferably the detector is arranged to capture data representative of the measurement of the physical or chemical property (e.g. of the concentration of the physical or chemical property) that the detector has detected (and to which the individual is exposed), i.e. at the locations in the environment that the individual wearing or carrying the portable device moves between.

The detector may be arranged to detect only a single type of physical or chemical property (e.g. contaminant). However in one embodiment the detector is arranged to measure multiple different physical or chemical properties (e.g. contaminants). Thus the detector may comprise a multi-channel detector.

The physical or chemical property may comprise any suitable and desired physical or chemical property associated with the environment, whose measurement is desired to be determined. Preferably the physical or chemical property comprises a contaminant, e.g. that is (or may be present) in the environment, and thus preferably the detector comprises a contaminant detector, e.g. arranged to detect the concentration of a contaminant which is or may be present in the environment and to which the individual is or may be exposed while in the environment.

The contaminant may comprise any substance that is or may be present in the environment and to which the individual is or may be exposed while in the environment, and, e.g., to which it is important to determine the exposure (e.g. total dose) of the individual owing to them being in the environment. For example, there may be recommended (or indeed legal) limits for the total (cumulative) dose to which an individual should be exposed while working in the environment.

In one set of embodiments the contaminant comprises radioactive material. Radioactive materials are conveniently detected by their emission of one or more of alpha particles, beta particles (electrons or positrons) and gamma radiation (photons). The radioactive materials may be present on surfaces in the environment and thus the individuals may be exposed to their decay products when they are in the environment.

As will be appreciated, the system and method of the present invention are particularly suited for determining the exposure of individuals to radioactive materials in an environment. This is because personal dosimeters are already commonplace to determine the exposure of an individual to radioactive material when working in a potentially contaminated environment. The portable device of the present invention thus improves on such dosimeters because the radiation dose to which an individual is exposed may be matched to the location at which the individual has been exposed to the radiation dose (and therefore at which radioactive material may be present) and/or correlated with the physiological parameter(s) of the individual carrying or wearing the portable device, e.g. using the data captured by the geolocation module and/or the physiological sensor(s). This helps to better ensure the safety of the individuals working the (e.g. potentially hazardous) environment.

The (e.g. contaminant) detector could comprise any suitable detector for detecting the physical or chemical property (e.g. contaminant) to be measured. However, as has been discussed above, the system of the present invention is particularly suitable for use in an environment which is potentially contaminated with radioactive material(s). Therefore in one set of embodiments the detector comprises a radiation monitor, e.g. an electronic personal dosimeter (e.g. including a MOSFET detector).

Typically radiation monitors detect a rate of decay of the radioactive materials, e.g. counts per second, and thus in one set of embodiments the data captured by the radiation monitor comprise a rate which is representative of the concentration of the radioactive decay products to which the individual is exposed while in the environment. This may allow both the total dose to which an individual is exposed, as well as the rate at any one time, to be determined.

In one set of embodiments the radiation monitor is arranged to detect the energy of the radioactive particles, e.g. preferably the radiation monitor comprises a radiation spectrometer. In this set of embodiments preferably the data captured by the radiation monitor comprise data representative of the energy of the radioactive particles detected by the radiation monitor. This may allow the total dose to which an individual is exposed to be determined.

The data captured by the detector may be recorded by and/or transmitted from the detector, e.g. to display a representation of the measurement of the physical or chemical property (e.g. of its concentration, rate, total dose, location, etc.) that the detector has detected, as will be described below.

The detector of each portable device may be arranged to measure the physical or chemical property at any suitable and desired sampling rate. For example, the detector may measure the physical or chemical property only once while the individual is in the environment but preferably it measures the property periodically or continuously.

Each portable device to be carried or worn in the environment by an individual includes one or more physiological sensors that measure a respective physiological parameter of the individual carrying or wearing the device while the individual is in the environment. Preferably each physiological sensor is arranged to capture data representative of the measurement of the physiological parameter that the physiological sensor has measured.

The physiological sensor(s) may comprise any suitable and desired sensors and may measure any suitable and desired physiological parameters. In one embodiment the physiological sensor(s) comprise one or more of: a temperature sensor (e.g. a thermometer, e.g. a thermistor) arranged to measure the temperature of the individual, a heart rate monitor arranged to measure the heart rate of the individual, and a step counter arranged to measure the number of steps the individual takes.

The physiological sensor(s) may be located in suitable and desired way with respect to the individual, e.g. depending on the physiological parameter to be measured. For example when the physiological sensor comprises a heart rate monitor, the heart rate monitor may comprise a wrist-based heart rate monitor or a chest-based heart rate monitor. A temperature sensor may be located similarly.

The one or more physiological sensors of each portable device may be arranged to measure the respective physiological parameter at any suitable and desired sampling rate. For example, the one or more physiological sensors may measure the respective physiological parameter only once while the individual is in the environment but preferably they measure the parameter periodically or continuously.

The geolocation module of each portable device is arranged to determine the location of the individual wearing or carrying the portable device in the environment. Preferably the geolocation module is arranged to capture data representative of the location at which the geolocation module has determined the portable device to be located.

The geolocation module may comprise any suitable and desired module to determine the location of the portable device (and thus the individual), e.g. depending on whether the environment is inside, outside or a mixture of the two. In one embodiment each geolocation module comprises a Global Navigation Satellite System (GNSS) receiver, e.g. to be used when the environment is at least partly outside.

In one embodiment the system comprises one or more (e.g. a plurality of) triangulation beacons positioned (e.g. in fixed location(s)) around the environment, wherein each triangulation beacon is arranged to transmit a wireless (e.g. Bluetooth) signal to (be received by) the plurality of portable devices in the environment, and each geolocation module comprises a receiver arranged to receive the wireless signal(s) transmitted by the triangulation beacon(s), wherein the geolocation module is arranged to use the received wireless signal(s) to determine the location of the individual (e.g. relative to the triangulation beacon(s)), e.g. using triangulation.

Preferably the triangulation beacon(s) are used when the environment is at least partly inside (and thus preferably the triangulation beacon(s) are positioned around an inside part of the environment). In a preferred set of embodiments the one or more triangulation beacons comprise one or more pseudolites. The triangulation beacon(s) (e.g. pseudolite(s)) help to provide a local, ground-based alternative to satellites (e.g. GNSS) for use in determining the location of the portable devices.

It will be appreciated that triangulation beacons may be used by the geolocation modules to determine the location of the respective portable devices (and thus the individuals), e.g. by using triangulation (e.g. of the respective strength of the wireless signals from the triangulation beacons) using the (preferably known) positions of the triangulation beacons. Preferably the respective locations of the portable devices are determined relative to the triangulation beacons.

Thus in one embodiment, e.g. when the environment comprises both indoor and outdoor regions, each geolocation module comprises a GNSS receiver and a receiver arranged to receive wireless signal(s) transmitted by the triangulation beacon(s). This allows the location of a portable device to be determined, when the individual moves around the environment between outdoor locations and indoor locations of the environment.

In one embodiment the system comprises one or more (e.g. a plurality of) communication units for communicating data collected by the portable devices with other(s) of the portable devices, with other(s) of the communication unit(s) and/or with the control unit, wherein the communication unit(s) are positioned (e.g. in fixed location(s)) around the environment. Thus preferably each communication unit comprises a transmitter and a receiver, e.g. a transceiver or a transmitter-receiver.

It will be appreciated that the communication unit(s), along with the (communication modules of the) portable devices, provide a communication network for communicating data between the communication unit(s) and the portable devices, and back to the control unit. This helps to allow data captured by the portable devices (and, e.g., the triangulation beacon(s) and/or the communication unit(s), as will be discussed below) to be transmitted back to the control unit, and also for the control unit to communicate with the portable devices, even when a portable device may be out of direct contact with the control unit. The communication unit(s) therefore provides a fixed communication network in addition to the portable devices to facilitate this transfer of data and thus reduce the likelihood that a particular portable device will fall outside the communication range of all of the other portable devices and the communication unit(s) while in the environment.

Thus, in a preferred embodiment, the system uses the network of portable devices and, e.g., communication unit(s) to transmit data captured by the portable devices to the control unit, e.g. via other portable devices and/or the communication unit(s). The control unit preferably transmits control signals to the portable devices (e.g. for the purposes of feedback, as will be discussed below) using the same network. With the network of portable devices and, e.g., communication unit(s) arranged in this way, a portable device wishing to transmit data to the control unit may, for example, simply transmit (e.g. broadcast) this data (e.g. indiscriminately), knowing that as long as the portable device is in range of another portable device or a communication unit, the data will be received by that portable device or communication unit and then retransmitted until it reaches the control unit.

While the triangulation beacon(s) are particularly useful when the environment is at least partly indoors, it will be appreciated that it may be beneficial for the system to comprise communication unit(s) throughout the whole of the environment, including when the environment is at least partly outdoors. In one set of embodiments one or more of the triangulation beacon(s) comprise a communication unit.

In a set of embodiments, at least one of the one or more triangulation beacons and/or at least one of the one or more communication units comprises at least one detector arranged to measure a chemical and/or a physical property associated with the environment. It will be appreciated that the data collected by the portable devices may not be sufficient to gather data over the whole of the environment, e.g. to produce an interpolated dose rate map. This may be because the environment covers a large area and/or only a small number of individuals (with portable devices) are present in the environment. The additional detector(s) of the triangulation beacon(s) and/or the communication unit(s) help to provide greater coverage for obtaining data of the chemical and/or physical properties of the environment.

The detector(s) of the triangulation beacon(s) and/or the communication unit(s) may comprise any suitable and desired detector(s). It will be appreciated that the detector(s) of the triangulation beacon(s) and/or the communication unit(s) may be of the same or different type of detector(s) as those of the portable devices. Therefore, preferably the features of the detector(s) of the portable devices described herein apply equally to the detector(s) of the triangulation beacon(s) and/or the communication unit(s).

Furthermore, preferably the communication unit(s) are arranged to communicate the data collected by the triangulation beacon(s) and/or the communication unit(s) data between the communication unit(s) and the portable devices, and back to the control unit. Thus, preferably the features of the communication unit(s) described herein in relation to the portable devices apply equally in relation to the triangulation beacon(s) and/or the communication unit(s).

The communication module of each of the portable devices allows data collected by the portable devices (and, e.g. the triangulation beacon(s) and/or the communication unit(s)) to be communicated back to the control unit, e.g. via other(s) of the plurality of portable devices and, for example, the communication unit(s). Preferably each communication module comprises a transmitter and a receiver, e.g. a transceiver or a transmitter-receiver.

Preferably the system is configured, and thus the communication modules are each arranged, to communicate the data collected by the portable devices (and/or, e.g., by the triangulation beacon(s) and/or by the communication unit(s)) back to the control unit. In a set of embodiments, the data collected is communicated to the control unit by a wired connection. In a set of embodiments, the data collected is communicated to the control unit by a wireless connection. This allows the control unit to process and analyse the data, as will be described further below.

Preferably each of the communication module(s) (and, e.g., each of the communication unit(s)) are arranged to communicate data collected by their portable device (and/or, e.g., by the triangulation beacon(s) and/or by the communication unit(s)) to one or more (e.g. all) of the other portable devices and/or to one or more (e.g. all) of the communication unit(s) (when provided), for communicating back to the control unit.

It will be appreciated that depending on the operational state of the system and/or the location of the individual (and thus the portable device), particularly if a localised communication protocol such as Bluetooth (RTM) is used, there may be times when a communication module or a communication unit is unable to communicate data to another communication module, to a communication unit (when provided) and/or to the control unit. (Preferably the communication unit(s) are positioned close enough to each other and/or to the control unit such that they are able to be in data communication with at least an adjacent communication unit and/or the control unit.)

Therefore, in a preferred embodiment, each portable device (and/or, e.g., each of the triangulation beacon(s) and/or the communication unit(s)) comprises a data storage module in data communication with the detector, the one or more physiological sensors and the geolocation module, wherein the data storage module is arranged to store data received from the detector, the one or more physiological sensors and the geolocation module. This local data storage (e.g. memory) allows data generated by a portable device to be stored (e.g. temporarily), e.g. until the communication module is able to transmit the data to the control unit (e.g. via other(s) of the portable device(s) and/or the communication unit(s) (when provided)).

The portable devices may be arranged to store data generated by the detector, the one or more physiological sensors and the geolocation module automatically. However in a preferred embodiment each portable device (and/or, e.g., each of the triangulation beacon(s) and/or the communication unit(s)) is arranged to store the data when it is determined that the communication module of the portable device is not in communication with any of the other communication modules, the communication unit(s) (when provided) and the control unit. Thus preferably each communication module (and/or, e.g., each of the triangulation beacon(s) and/or the communication unit(s)) is arranged to determine when it is not in communication with any of the other communication modules, the communication unit(s) (when provided) and the control unit, and arranged to store the data accordingly.

The communication modules (and/or, e.g., each of the triangulation beacon(s) and/or the communication unit(s)) may each determine that they are not in communication with any of the other communication modules, the communication unit(s) (when provided) and the control unit in any suitable and desired way. For example, a communication module (and/or, e.g., a triangulation beacon and/or a communication unit) may determine that it is not in data communication owing to its location (e.g. determined using GNSS) and/or owing to it not receiving data from any of the other communication modules, the communication unit(s) (when provided) and the control unit.

Conversely, in these embodiments, when the communication module (and/or, e.g., the triangulation beacon and/or the communication unit) is in communication with at least one of the other communication modules, the communication unit(s) (when provided) and/or the control unit, the communication module is arranged to transmit data generated by the detector, the one or more physiological sensors and the geolocation module. Thus, in one embodiment each of the communication modules (and/or, e.g., each of the triangulation beacon(s) and/or the communication unit(s)) is arranged to determine when it is in communication with at least one of the other communication modules, the communication unit(s) (when provided) and/or the control unit. This may simply be that the communication module (and/or, e.g., the triangulation beacon and/or the communication unit) is receiving data from at least one of the other communication modules, the communication unit(s) (when provided) and/or the control unit, or that an acknowledgement (e.g. handshake) is transmitted when data is received successfully by another communication module, a communication unit (when provided) or the control unit.

When a communication module (and/or, e.g., the triangulation beacon and/or the communication unit) is unable to communicate data to another communication module, to a communication unit (when provided) and/or to the control unit (and thus preferably stores the data in the data storage of the portable device), preferably the communication module (and/or, e.g., the triangulation beacon and/or the communication unit) is arranged to transmit the (stored) data when (e.g. at a subsequent time it is determined that) the communication module (and/or, e.g., the triangulation beacon and/or the communication unit) is able to communicate data to another communication module, to a communication unit (when provided) and/or to the control unit.

In this manner, the captured data is able to be transmitted back to the control unit, e.g. via one or more intermediate communication modules of portable devices and/or one or more communication units. Preferably if any of these intermediate modules or units are unable to transmit the data (e.g. owing to being out of the range of other portable devices, communication units and the control unit) the data is stored and the module or unit reattempts to transmit the data at a subsequent time, i.e. in the same manner as the original portable device.

Thus preferably the method comprises a communication module of a portable device (and/or, e.g., a triangulation beacon and/or a communication unit) determining when it is in communication with at least one of the other communication modules, the communication unit(s) (when provided) and/or the control unit, and when the communication module of the portable device (and/or, e.g., the triangulation beacon and/or the communication unit) is in communication with at least one of the other communication modules, the communication unit(s) (when provided) and/or the control unit: the communication module (and/or, e.g., the triangulation beacon and/or the communication unit) transmitting data captured by the portable device; and when the communication module of the portable device (and/or, e.g., the triangulation beacon and/or the communication unit) is not in communication with any of the other communication modules, the communication unit(s) (when provided) and the control unit, the data storage of the portable device (and/or, e.g., of the triangulation beacon and/or of the communication unit) storing the captured data.

Preferably the method comprises a communication module of another portable device or a communication unit (when provided) receiving the captured data from the portable device (and/or, e.g., the triangulation beacon and/or the communication unit) (or from an intermediate portable device or communication unit) and retransmitting the captured device. Again, as outlined above, preferably the intermediate (communication module of the) portable device or communication unit determines first whether or not it is in communication with at least one of the other communication modules, the communication unit(s) (when provided) and/or the control unit, and retransmitting or storing the data accordingly. Preferably the data is retransmitted repeatedly in the same manner until it is received by the control unit.

In one embodiment each portable device comprises a feedback module arranged to provide feedback to the individual wearing or carrying the portable device. The feedback may be based on any suitable and desired data that the components of the portable device (or of other portable devices) have captured. Preferably the feedback a particular portable device provides is based on (e.g. analysis of) the data captured by that portable device.

The feedback that a particular portable device provides may be controlled by that portable device itself, e.g. when the feedback is based on the data captured by that portable device. For example, each portable device may provide feedback to the individual when the chemical or physical property measured reaches (or exceeds) a particular threshold. Thus preferably each device is arranged to determine (from the measurements of the chemical or physical property by the detector) the cumulative exposure of the individual to the chemical or physical property (e.g. cumulative dose) associated with the environment.

The feedback (e.g. a particular threshold, such as a received dose) may be set based on the individual to which the feedback is to be provided and/or on the task that the individual is performing in the environment and/or on the (e.g. physiological) data captured by the portable device the individual is wearing or carrying. This allows the feedback to be personalised and tailored to an individual, their work in the environment and/or their physiological state.

In another embodiment the feedback is controlled by the control unit, e.g. the control unit is arranged to transmit a signal to the portable device(s), e.g. following analysis of the captured data. Thus preferably the control unit is arranged to analyse the data captured by the portable device(s) and provide feedback control signal(s) to the portable device(s) based on the analysis of the captured data, wherein the feedback module(s) of the portable device(s) are arranged to provide feedback to the respective individuals when they receive the control signal(s).

The feedback module may provide feedback in any suitable and desired way. For example, the feedback module may provide visual, audio and/or haptic feedback to the individual. Thus the feedback module may comprise a visual, audio and/or haptic output which is arranged to provide feedback to the individual. A haptic output is particularly convenient for the portable device that is carried or worn by an individual, e.g. the haptic output may be provided in a wrist strap (e.g. a bracelet or watch).

In one embodiment, e.g. when the control unit performs mapping and/or visualisation of the captured data (as will be discussed below), the feedback module comprises an augmented reality output (e.g. a head-up display).

Preferably (e.g. all of) the data captured and transmitted over the system is encrypted, e.g. using end to end encryption. Thus, in one embodiment, one or more (e.g. preferably all) of the portable devices, the detectors, the physiological sensors, the geolocation modules, the communication modules, the feedback modules, the communication unit(s), the triangulation beacon(s), the data storage modules (and any such other components of the portable devices and the system) are arranged to encrypt the data they capture, transmit and receive (as appropriate).

The invention also extends to the portable device per se and thus when viewed from a further aspect the invention provides a portable device for monitoring the exposure of an individual to a physical or chemical property associated with an environment, wherein the portable device is arranged to be worn or carried by an individual in the environment, and wherein the portable device comprises:

a detector arranged to measure a physical or chemical property that the individual wearing or carrying the device is exposed to in the environment;

one or more physiological sensors each arranged to measure a physiological parameter of the individual;

a geolocation module arranged to determine the location of the individual; and a communication module for transmitting data collected by the portable device from the portable device.

As will be appreciated by those skilled in the art, this aspect of the present invention can, and preferably does, include any one or more or all of the preferred and optional features of the present invention discussed herein, as appropriate. In particular, the portable device may comprise a data storage.

The control unit is arranged to be able to communicate with each of the (communication modules of the) plurality of portable devices (e.g. when they are in range) (and/or, e.g., the triangulation beacon(s) and/or the communication unit(s)).

Thus preferably the control unit comprises a receiver and, e.g. a transmitter, e.g. a transceiver or a transmitter-receiver. Preferably the control unit comprises a data storage arranged to store data received by the control unit.

It will be appreciated that with the data captured by the portable devices (and/or, e.g., by the triangulation beacon(s) and/or by the communication unit(s)), and transmitted back to the control unit, the control unit may then be able to use the data to provide real-time localisation of the individuals in the environment and to provide real-time information regarding their exposure to the chemical or physical property associated with the environment.

Preferably the control unit is arranged to use the captured and received data to generate, e.g., maps and/or visualisations of the captured data and its respective locations in the environment, e.g. for one or more of the individuals spending time in the environment. Preferably the control unit is arranged to provide this mapping and/or visualisation in real time and/or automatically. This (e.g. automatic) generation of geospatial information (i.e. the captured data matched with location data associated with the captured data) helps to output the captured data in an easily understood format.

Thus, in a set of embodiments, the control unit is arranged to generate (and the method comprises generating) an output from the data collected by the portable devices (and/or, e.g., by the triangulation beacon(s) and/or by the communication unit(s)). An exemplary output is a map of the environment with the locations and data received from various portable devices (and/or, e.g., from the triangulation beacon(s) and/or from the communication unit(s)) within the environment plotted on the map. This output may then be used to optimize and plan operations.

Additionally or alternatively, the output from the captured data comprises an interpolated dose rate map of the environment, e.g. where regions on the map are coloured according to the values of the captured data in that region. The output from the captured data may change as the captured data varies, and therefore the output can vary with time. Communicating the captured data to the control unit and the control unit generating an output based on the captured data allows the information to be centralized. This information can then be monitored and analysed to optimize and plan, e.g., the operation of workers in a radioactive environment.

In one embodiment the control unit provides the mapping and/or visualisation to the portable device having captured the data used to generate the mapping and/or visualisation. This may be done in any suitable and desired way, e.g. using the feedback module outlined above and the control unit transmitting control signals thereto. The mapping and/or visualisation (e.g. of the data representative of the detected chemical or physical property) may be presented to the individual wearing or carrying the portable device along with the captured physiological data.

The portable device and/or the control unit (and/or each of their components) may comprise processing circuitry (e.g. a CPU) to perform the outlined (e.g. data processing) functions of the respective portable device and/or the control unit (and/or each of their components (e.g. modules)).

A preferred embodiment of the invention will now be described, by way of example only, with reference to the accompanying drawings in which.

When working in a nuclear facility (e.g. a nuclear power plant), it is important to measure accurately the exposure of individuals working in the environment of the facility to radioactive materials that may be present in the environment. An embodiment of the present invention, which will now be described, provides a system for monitoring the exposure of such individuals to radioactive materials. This helps to ensure that the individuals are not each exposed to a potentially harmful cumulative dose of radiation.

Figure 1:
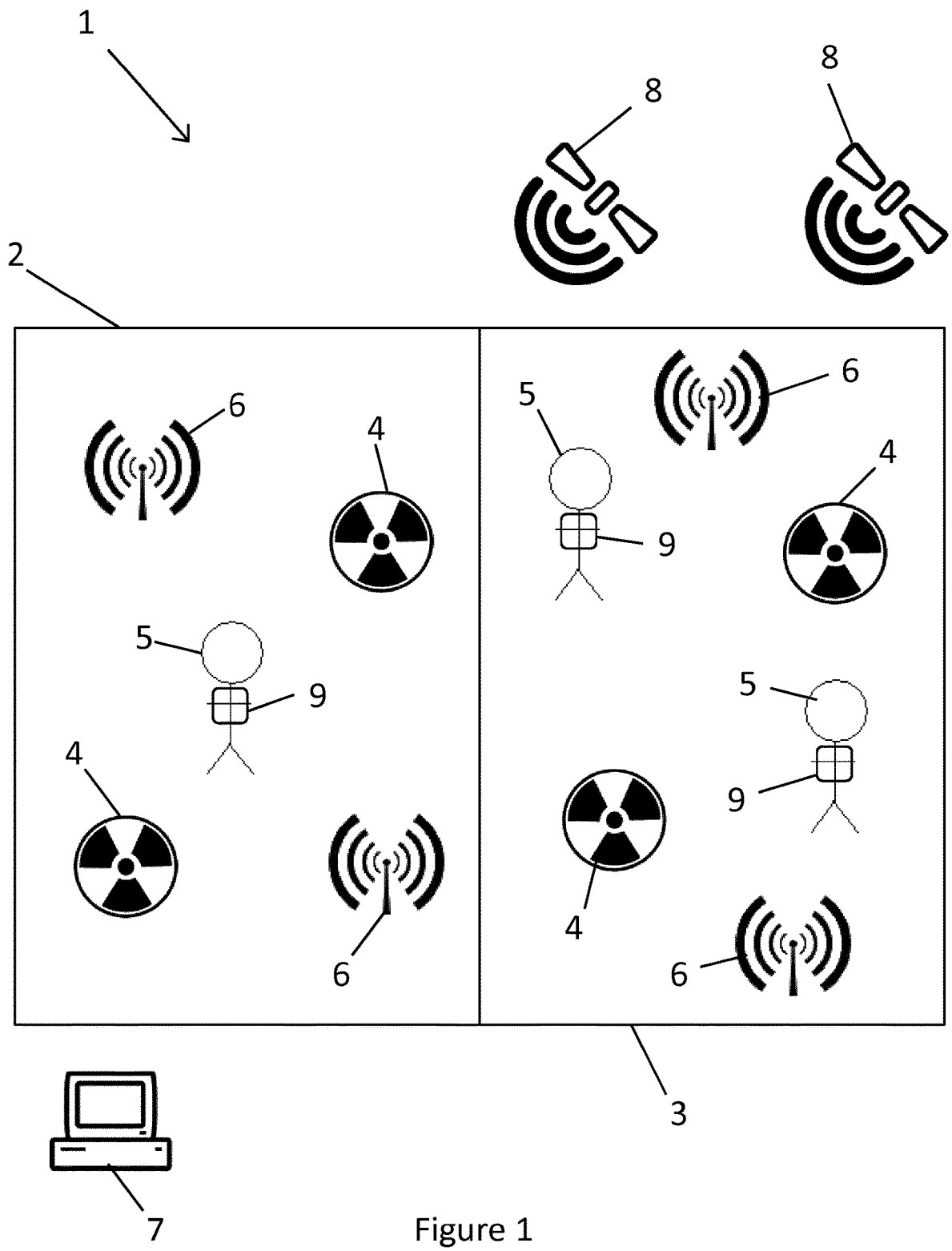
FIG. 1 shows schematically a monitoring system according to a preferred embodiment of the present invention.

FIG. 1 shows schematically an overview of a monitoring system 1 according to an embodiment of the present invention. The system 1 is implemented in an indoor area 2 and an outdoor area 3 of an environment. The indoor and outdoor areas 2, 3 together form an environment in a nuclear facility in which radioactive materials 4 are present. Thus individuals (e.g. workers) 5 spending time in the indoor and outdoor areas 2, 3 of the environment are exposed to the decay products (e.g. alpha, beta and/or gamma radiation) of the radioactive materials 4.

Multiple fixed units 6 are positioned at fixed, known locations in the indoor and outdoor areas 2, 3 of the environment. As will be described with reference to FIG. 2, these fixed units 6 are arranged to be in data communication with any individuals who are in the indoor and outdoor areas 2, 3. The system 1 also includes a control unit 7 arranged to be in data communication with one or more of the individuals 5 and one or more of the fixed units 6.

In the outdoor area 3 of the environment the individuals 5 are able to be visible to GNSS (e.g. GPS and/or GLONASS) satellites 8.

When in the indoor and outdoor areas 2, 3 of the environment, the individuals 5 carry or wear a portable device 9. The functions of the portable device 9, as well as the fixed units 6 and the control unit 7 will now be described with reference to FIG. 2.

Figure 2:
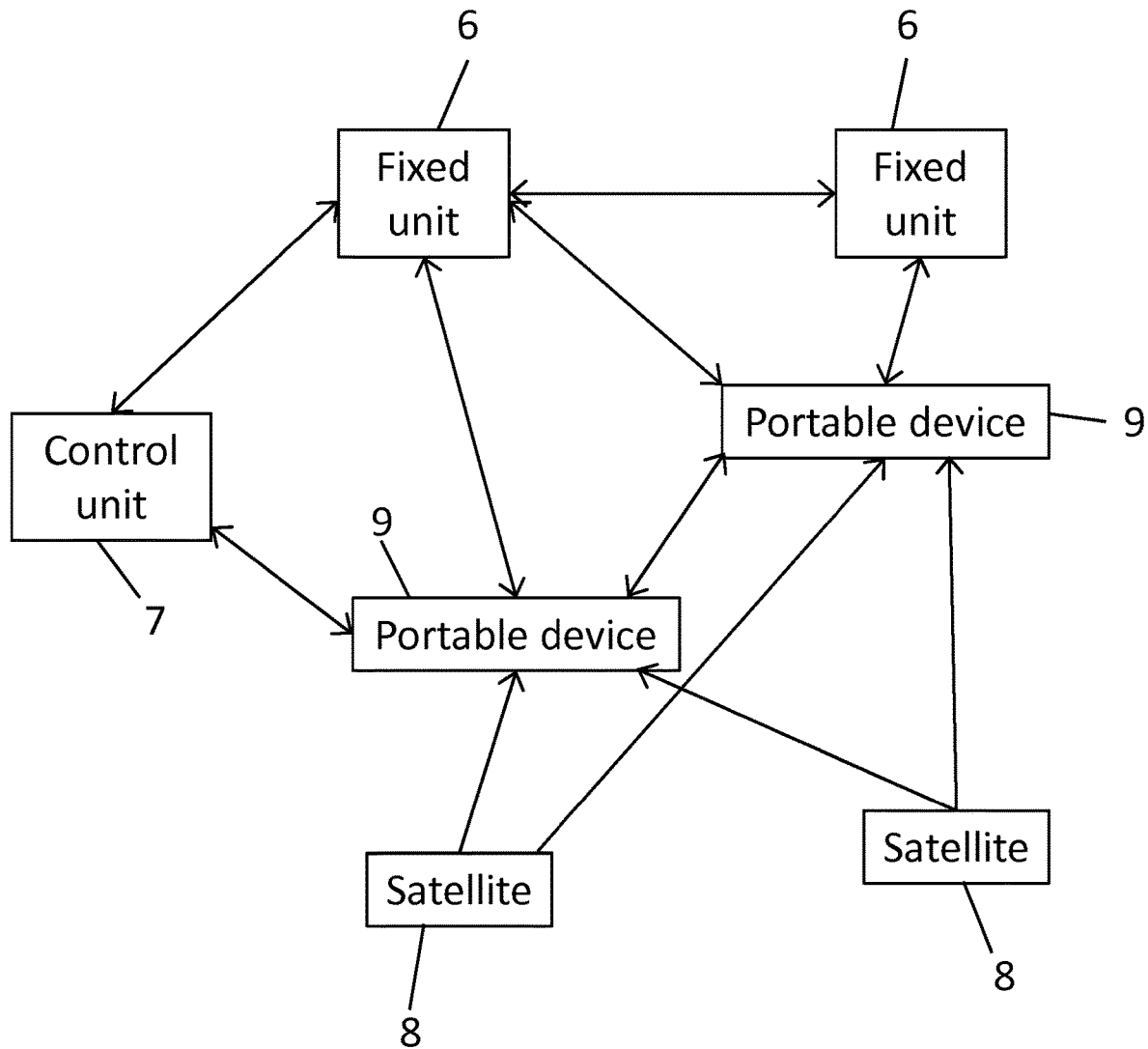
FIG. 2 shows schematically the components of the system shown in FIG. 1.

FIG. 2 shows schematically the components of the system 1 shown in FIG. 1 and their interactions with each other. The portable devices 9 are in wireless communication with each other, with the control unit 7 and with the fixed units 6, as long as they are in range (for example, one of the portable devices 9 shown in FIG. 2 is not directly in communication with one of the fixed units 6). The portable devices 9 also receive geolocation signals from GNSS satellites 8 (when they are outside). The fixed units 6 are in wireless communication with each other and with the control unit 7 (when in range).

Figure 3:
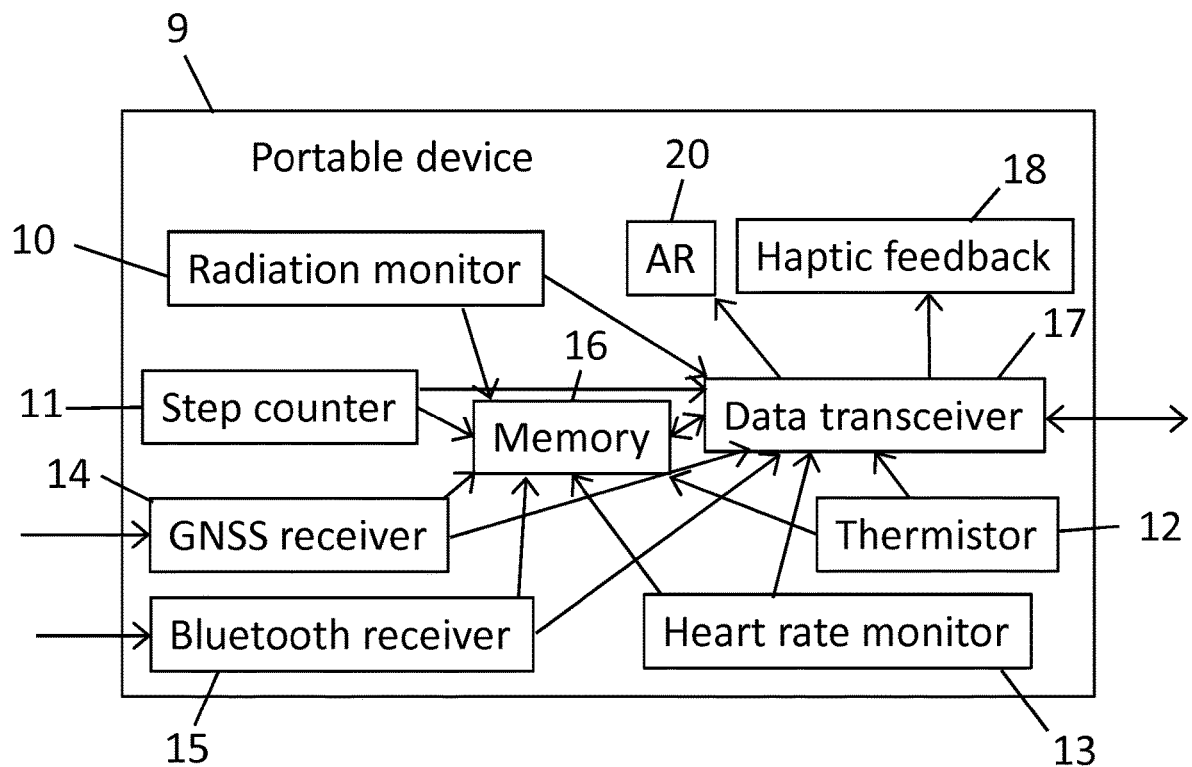
FIG. 3 shows schematically a portable device to be used in the system shown in FIGS. 1 and 2.

FIG. 3 shows schematically the components of a portable device 9 to be used in the system 1 shown in FIGS. 1 and 2. The portable device 9 includes a radiation monitor 10 arranged to monitor the exposure of an individual wearing and carrying the portable device 9 to radioactive materials in the environment.

The portable device 9 also includes a number of physiological sensors. A step counter 11 is arranged to measure the number of steps the individual wearing and carrying the portable device 9 takes (while in the environment). A thermistor 12 is arranged to measure the temperature of the individual wearing and carrying the portable device 9 (while in the environment). A heart rate monitor 13 is arranged to measure the heart rate of the individual wearing and carrying the portable device 9 (while in the environment).

The heart rate monitor 13, which may, for example, be a Polar H10 heart rate monitor, may be fixed to the chest of the user with a strap. Such a heart rate monitor 13 is equipped with two electrodes for measuring the heart rate using electrocardiogram technology. The data from the electrodes may be processed with suitable measuring algorithms. The heart rate monitor 13 may then use Bluetooth Low Energy (BLE) to transmit this data in real time to the memory 16 and the data transceiver 17 of the portable device 9 using a BLE transmitter and receiver (not shown). The heart rate monitor 13 may use a standard Generic Attribute Profile (GATT), which may provide an easier format for data and with the profile demonstrating good autonomy (e.g. up to 400 hours). The heart rate monitor 13 may also have a built-in memory, which in case of disconnection from the rest of the paired portable device 9 allows the heart rate monitor 13 to store the data (e.g. for the length of one shift) and transmit the data upon reconnection.

The portable device 9 includes a geolocation module made up of a GNSS receiver 14 (arranged to receive geolocation signals from GNSS satellites 8) and a Bluetooth receiver 15 (arranged to receive Bluetooth signals from the fixed units 6 shown in FIGS. 1 and 2). This allows the portable device 9 to determine its location, either from the geolocation signals from the GNSS satellites 8 or from the Bluetooth signals from the fixed units 6.

Each of the described components of the portable device 9 is in data communication with a memory 16 and with a data transceiver 17. The memory 16 is arranged to store data captured by the components of the portable device 9 and the data transceiver 17 is arranged to transmit data from the portable device 9 (to other portable devices 9, to the fixed units 6 and/or to the control unit 7 shown in FIGS. 1 and 2 (when in range)). The data transceiver 17 is similarly arranged to receive data from the other portable devices 9, the fixed units 6 and/or the control unit 7 shown in FIGS. 1 and 2 (when in range).

The portable device 9 also includes a haptic feedback module 18 in communication with the data transceiver 17 and arranged to provide feedback to the individual wearing and carrying the portable device 9. The portable device 9 further includes an AR display 20, e.g. a pair of ORA-2 glasses. The AR display 20 is in communication with the data transceiver 17, e.g. via a BLEnergy protocol.

Figure 4:
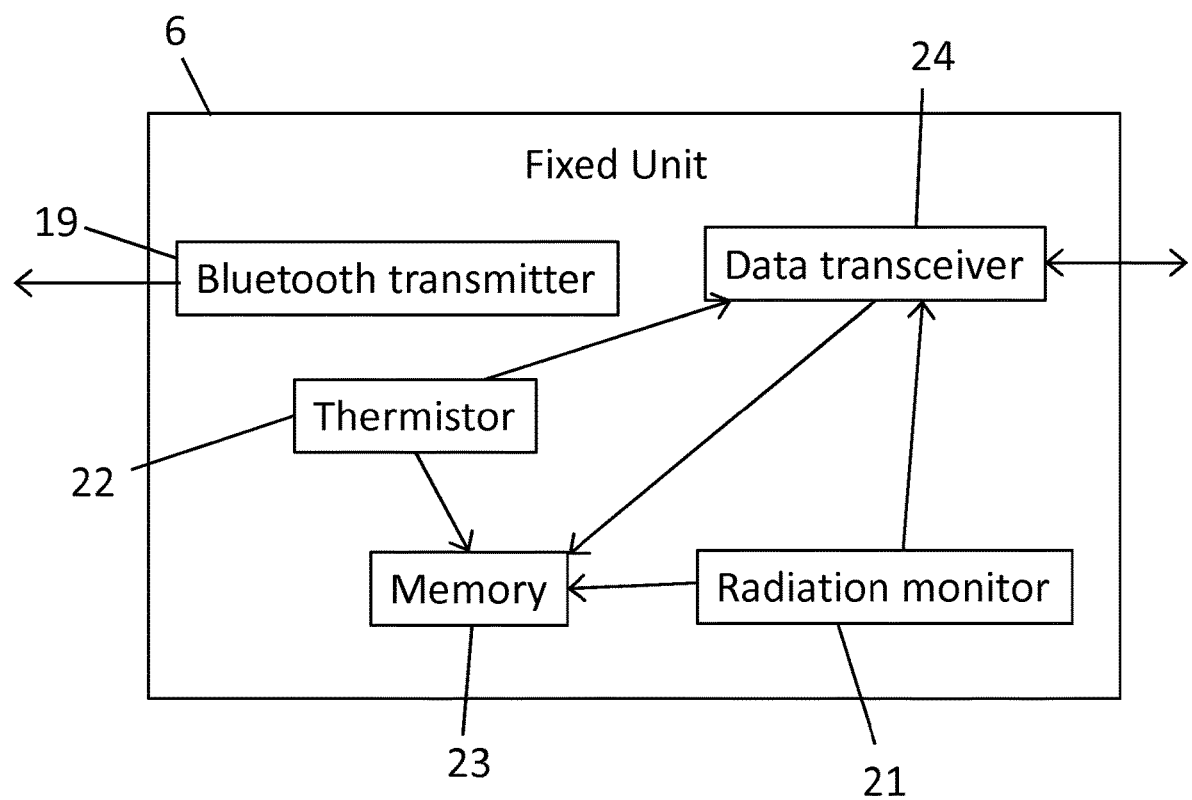
FIG. 4 shows schematically a fixed unit to be used in the system shown in FIGS. 1 and 2.

FIG. 4 shows schematically the components of a fixed unit 6 to be used in the system 1 shown in FIGS. 1 and 2. The fixed unit 6 includes a Bluetooth transmitter 19 arranged to transmit Bluetooth signals (for use by the portable devices 9 to determine their location, e.g. relative to the fixed unit 6).

The fixed unit 6 also includes a radiation monitor 21 arranged to monitor the levels of radioactive materials in the environment in the vicinity of the fixed unit 6 and a thermistor 22 arranged to measure the temperature in the environment in the vicinity of the fixed unit 6.

The fixed unit 6 includes a memory 23 and a data transceiver 24. The memory 23 is arranged to store data captured by components of, or transmitted to, the fixed device 6, and the data transceiver 24 is arranged to transmit data from the fixed unit 6 (to the portable devices 9, to other fixed units 6 and/or to the control unit 7 shown in FIGS. 1 and 2 (when in range)). The data transceiver 24 is similarly arranged to receive data from the portable devices 9, the other fixed units 6 and/or the control unit 7 shown in FIGS. 1 and 2 (when in range).

Figure 5:
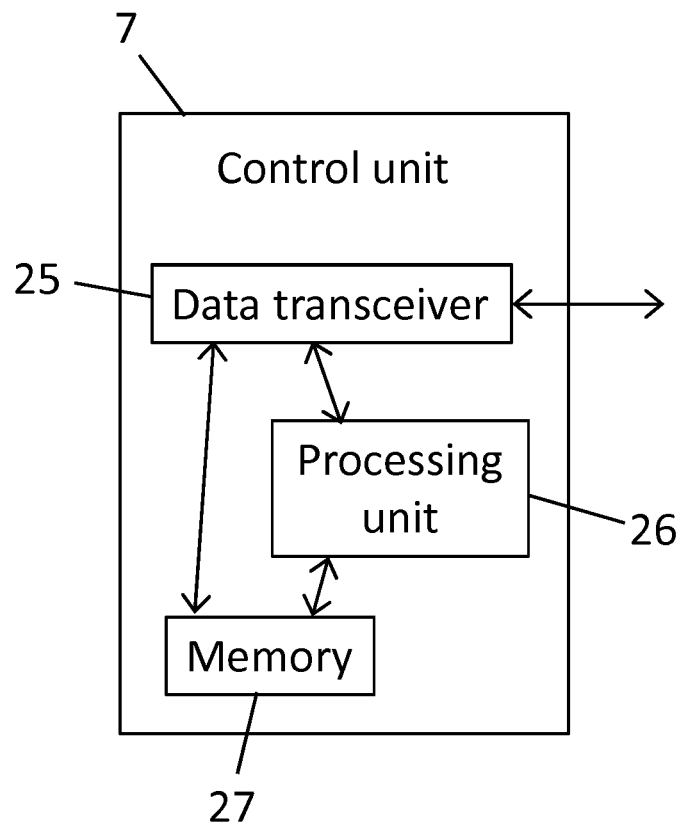
FIG. 5 shows schematically a control unit to be used in the system shown in FIGS. 1 and 2.

FIG. 5 shows schematically the components of a control unit 7 to be used in the system 1 shown in FIGS. 1 and 2.

The control unit 7 includes a data transceiver 25 which is arranged to receive data from the portable devices 9 and fixed units 6 of the system 1. The data transceiver is also arranged to transmit data (e.g. control signals) to the portable devices 9 and fixed units 6 of the system 1. The control unit 7 also includes a processing unit (e.g. CPU) 26 and a memory 27, which are in data communication with each other and with the data transceiver 25.

Operation of the system 1 will now be described using the flow chart of FIG. 6 and with reference to FIGS. 1 to 5.

When individuals 5 are to enter the environment (e.g. including the inside and outside areas 2, 3), the individuals 5 put on their portable devices 9 (step 101, FIG. 6), which they wear or carry while in the environment. The individuals 5 enter the environment and perform the tasks they have to perform while in the environment. While the individuals 5 are in the environment, the radiation monitor of each portable device 9 measures the exposure of the respective individual 5 to radioactive materials, the step counter 11 measures the number of steps the individual 5 takes while in the environment, the thermistor 12 measures the temperature of the individual 5 and the heart rate monitor 13 measures the heart rate of the individual 5 (step 102, FIG. 6). The fixed devices 6 also measure radioactivity using their radiation monitors 21 and temperature using their thermistors 22. These measurements are sampled periodically and frequently during the time the individuals 5 are in the environment.

Figure 6:
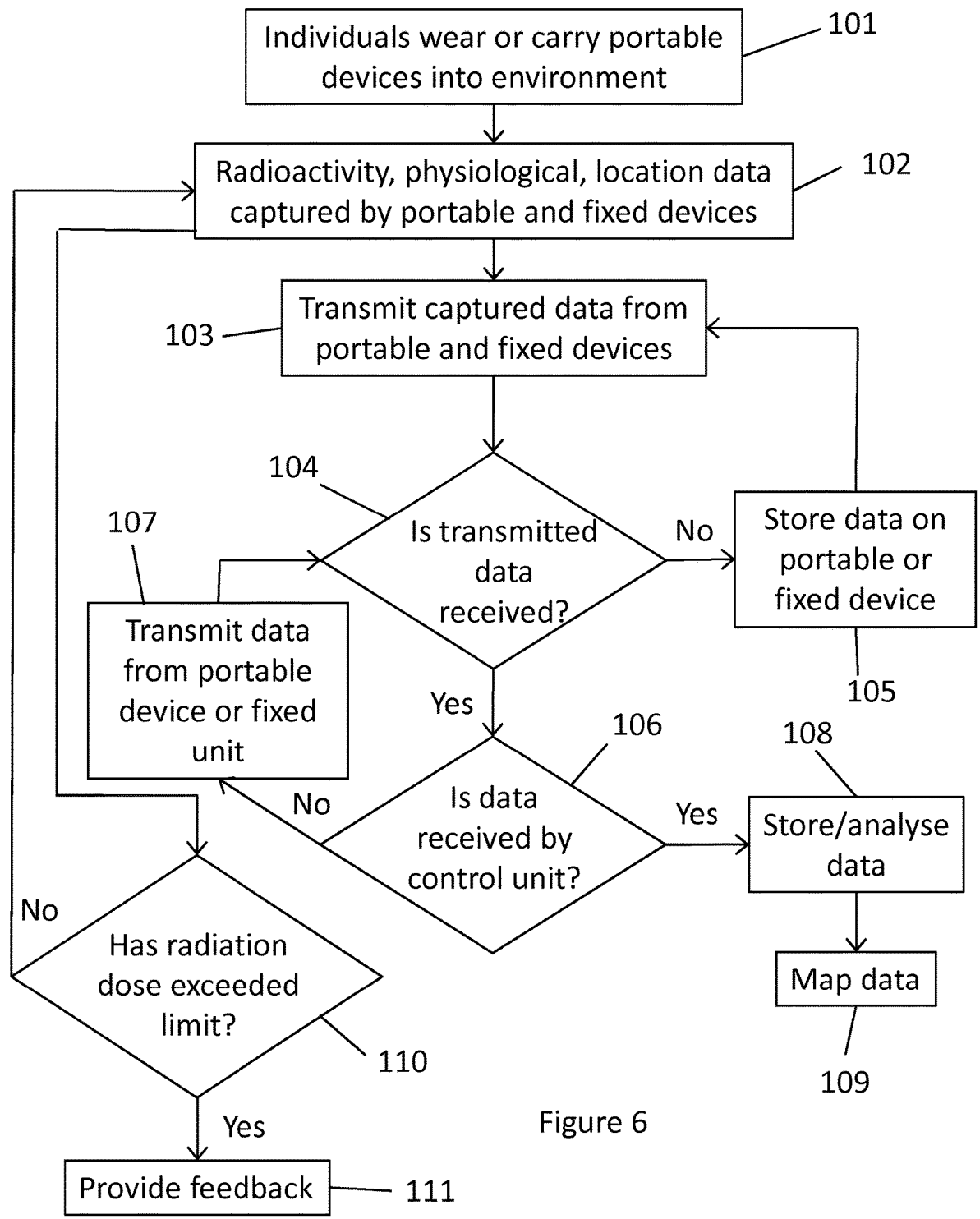
FIG. 6 shows a flow chart of the operational steps of the system shown and its components shown in FIGS. 1 to 5.

At the same time as the individual's exposure to radioactive material and their physiological parameters are being measured, while the individual is in the environment, the location of the portable device (step 102, FIG. 6). This is done by the GNSS receiver 14 receiving geolocation signals from GNSS satellites 8 and/or the Bluetooth receiver 15 receiving Bluetooth signals from the Bluetooth transmitters 19 in the fixed units 6, and (e.g. a processor of) the portable device 9 using these signals to determine the location of the portable device 9 (and thus the individual 5) in the environment, e.g. relative to the fixed units 6.

Periodically the portable devices 9 and the fixed devices 6 transmit their captured and determined data (as end to end encrypted data) from the portable devices 9 and the fixed devices 6 via their respective data transceivers 17, 24 (step 103, FIG. 6) to be received by others of the portable devices 9, by the fixed units 6 (via their data transceivers 24) or by the control unit 7 (via its data transceiver 25) of the system 1. When data is received successfully, an acknowledgement is sent to the portable device 9 or the fixed device 6 transmitting the data, thus allowing the portable device 9 or the fixed device 6 to confirm whether or not the transmitted data has been received (step 104, FIG. 6).

If the transmitted data has not been received by any others of the portable devices 9, the fixed units 6 or the control unit 7 (e.g. owing to the portable device 9 being out of range from the other portable devices 9, the fixed units 6 and the control unit 7), the data is stored in the memory 16 of the portable device 9 or the fixed device 6 (step 105, FIG. 6). At a later time, the stored data is transmitted again (e.g. along with any data captured by the portable device 9 or the fixed device 6 in the meantime) (step 103, FIG. 6) and again it is determined if the transmitted data has been received (step 104, FIG. 6).

When the transmitted data is received (e.g. at the first or subsequent attempts) by others of the portable devices 9, the fixed units 6 or the control unit 7, the portable device 9 or the fixed device 6 determines whether or not this data has been received by the control unit 7 (step 106, FIG. 6). If the data has not been received by the control unit 7, the data is retransmitted by the portable device 9 or the fixed unit 6 that received the initially transmitted data (step 107, FIG. 6). In this way, the data can be transmitted via one or more portable devices 9 and fixed units 6 such that it is eventually relayed back to the control unit 7.

When the data is received by the control unit 7, the control unit 7 then stores the data in its memory 27 and the data is analysed by the processing unit 26 of the control unit 7 (step 108, FIG. 6). This allows the captured data to be mapped (i.e. using the radiation and the physiological measurements matched to the determined locations) such that it can be visualised (step 109, FIG. 6).

While the data is being captured by the portable devices 9, each portable device determines the cumulative radiation dose to which the individual 5 wearing or carrying the portable device 9 has been exposed, using the captured radiation data (step 110, FIG. 6). If the recommended or legal limit for the individual has not been reached, the individual is permitted to remain working in the environment and the portable device 9 continues to capture data (step 102, FIG. 6).

If the recommended or legal limit for the individual has been reached, the haptic feedback module 18 is used to provide a haptic output to the individual 5 (step 111, FIG. 6), alerting the individual 5 that it is required for them to cease work and exit the environment.

Figure 7:
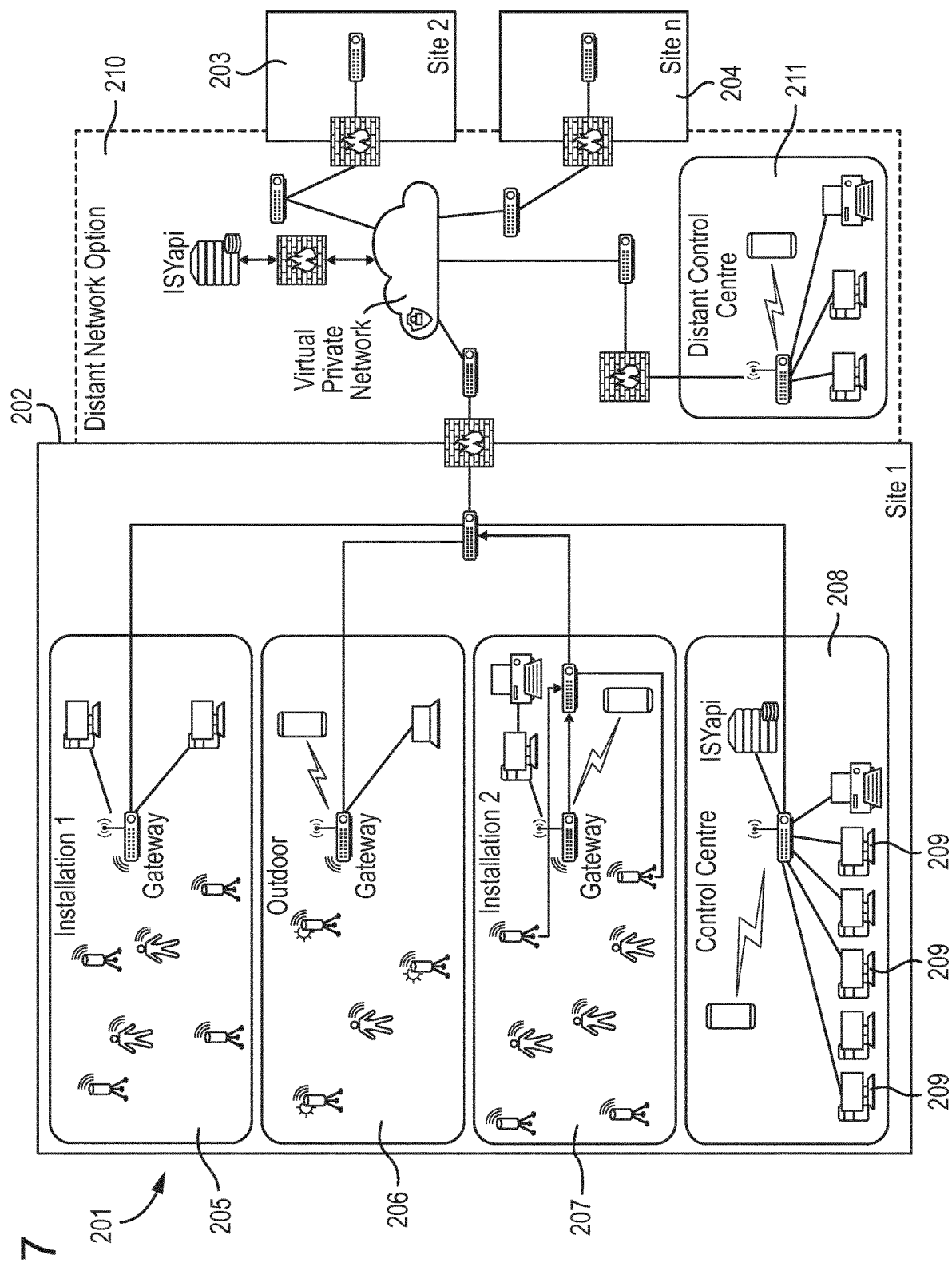
FIG. 7 shows an embodiment of the system that is deployed at various facilities and sites.

FIG. 7 shows an embodiment of the system 201 that is deployed at various facilities and sites 202, 203, 204. Each facility or site may be embodied as shown in FIGS. 1-6, for example. Thus, as shown in FIG. 7, one of the sites "Site 1" 202 includes various different indoor and outdoor zones 205, 206, 207. Each zone 205, 206, 207 may include local control units for the local processing of data, as well as transmitter (s) for transmitting the data to a network. The site 202 also includes a control centre 208 in which, inter alia, multiple control units 209 are located.

The information and data collected at each site 202, 203, 204 is transmitted via a network 210 to a central control centre 211. This network 210 is not required to be localized at any site or facility. The control centre 211 may analyse the data centralized in the network 210 from the various sites and facilities 202, 203, 204. Monitoring and control in order to optimize performance at individual sites 202, 203, 204 is performed by the control centre 211.

The control centre 211 may be remote from any number of the facilities and sites 202, 203, 204 being monitored. As any number of additional sites and facilities 202, 203, 204 implementing the system as described herein may be connected to the network 210 and control centre 211, the system is inherently scalable and interoperable. Such wide monitoring of a number of sites 202, 203, 204 has previously been unavailable.

Figure 8:
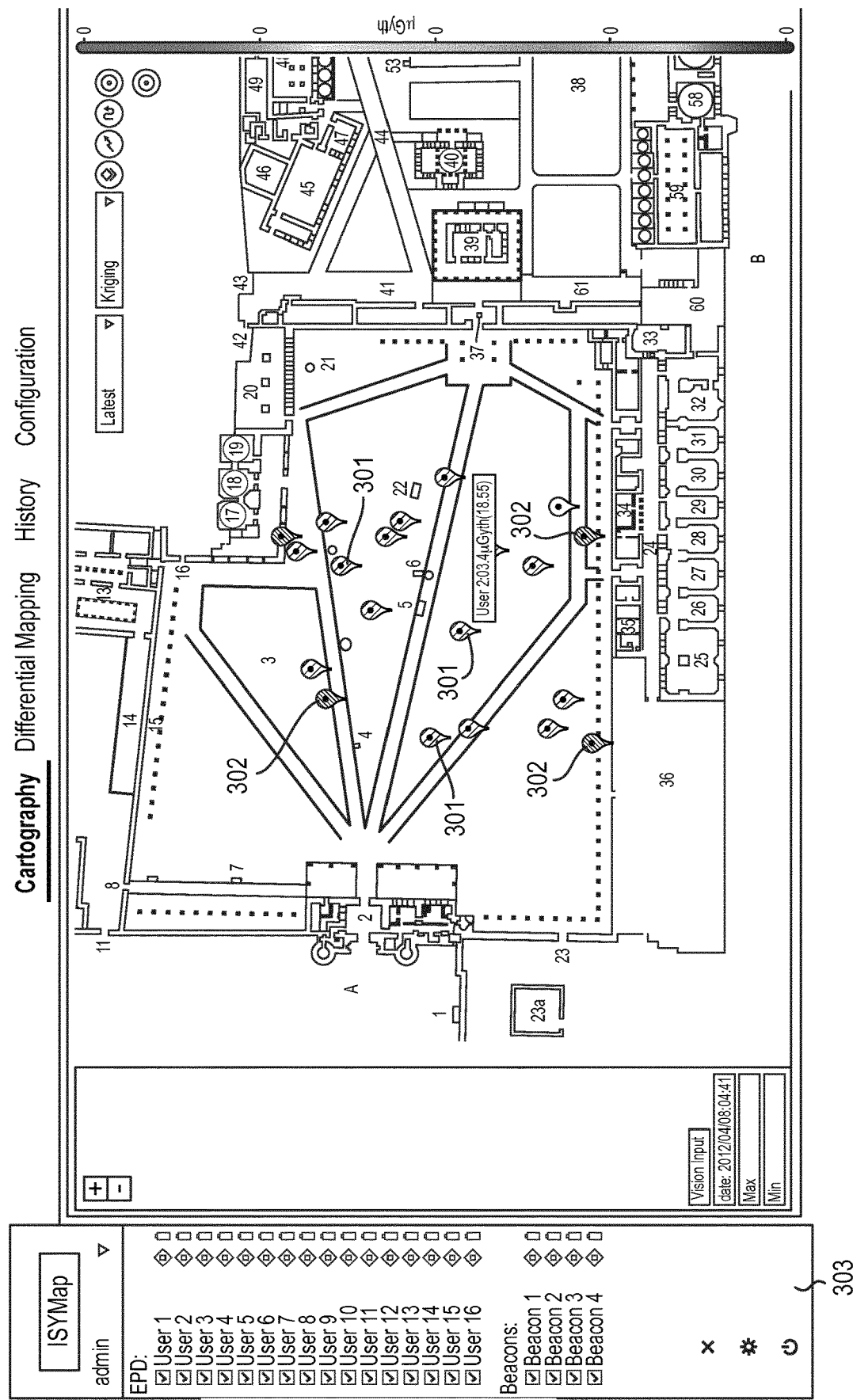
FIG. 8 shows an exemplary map produced using the data acquired from a system in accordance with an embodiment of the present invention.

FIG. 8 shows an exemplary map produced using the data acquired from the portable devices 301 and fixed devices 302 (e.g. triangulation beacons) of a system in accordance with an embodiment of the present invention. The map shows the positions of portable devices 301 (indicating the positions of individuals) and the positions of the triangulation beacons 302. The individuals within the environment mapped are labelled according to the radiation dose rate they are exposed to. For example, different colours may be used to indicate the differing dose rates experienced by different users. The positions of the triangulation beacons 302 may also be shown on the map. The triangulation beacons 302 shown on the map in FIG. 8 also include radiation detectors, therefore the triangulation beacons 302 are similarly labelled (e.g. with different colours) according to the dose rate recorded. The map may also include a legend 303 showing a list of the different portable devices 301 and fixed devices 302.

Figure 9:
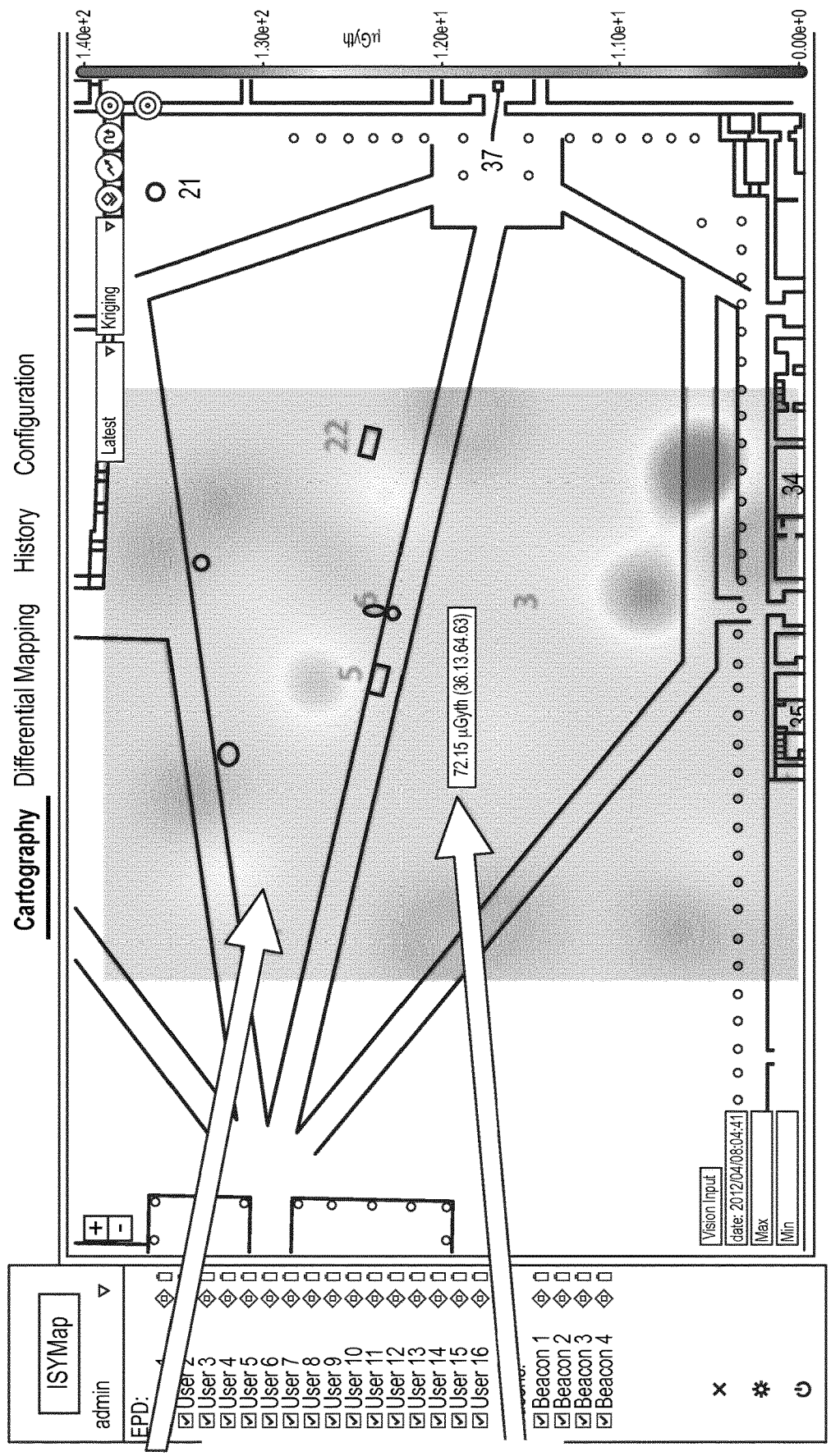
FIG. 9 shows another exemplary map produced using the data acquired from a system in accordance with an embodiment of the present invention.

FIG. 9 is another exemplary map produced using the data acquired from the portable devices and triangulation beacons (e.g. from the installation shown in FIG. 8). In FIG. 9, rather than the positions and the associated dose rates of individual portable devices and triangulation beacons being overlaid on a map of the environment, a colour-contour plot is generated by interpolated the data from the portable devices and triangulation beacons. In a computer based implementation, selecting a certain point on the colour-contour plot overlaid onto the map may produce a readout of the exact dose rate interpolated at that point.

Figure 10:
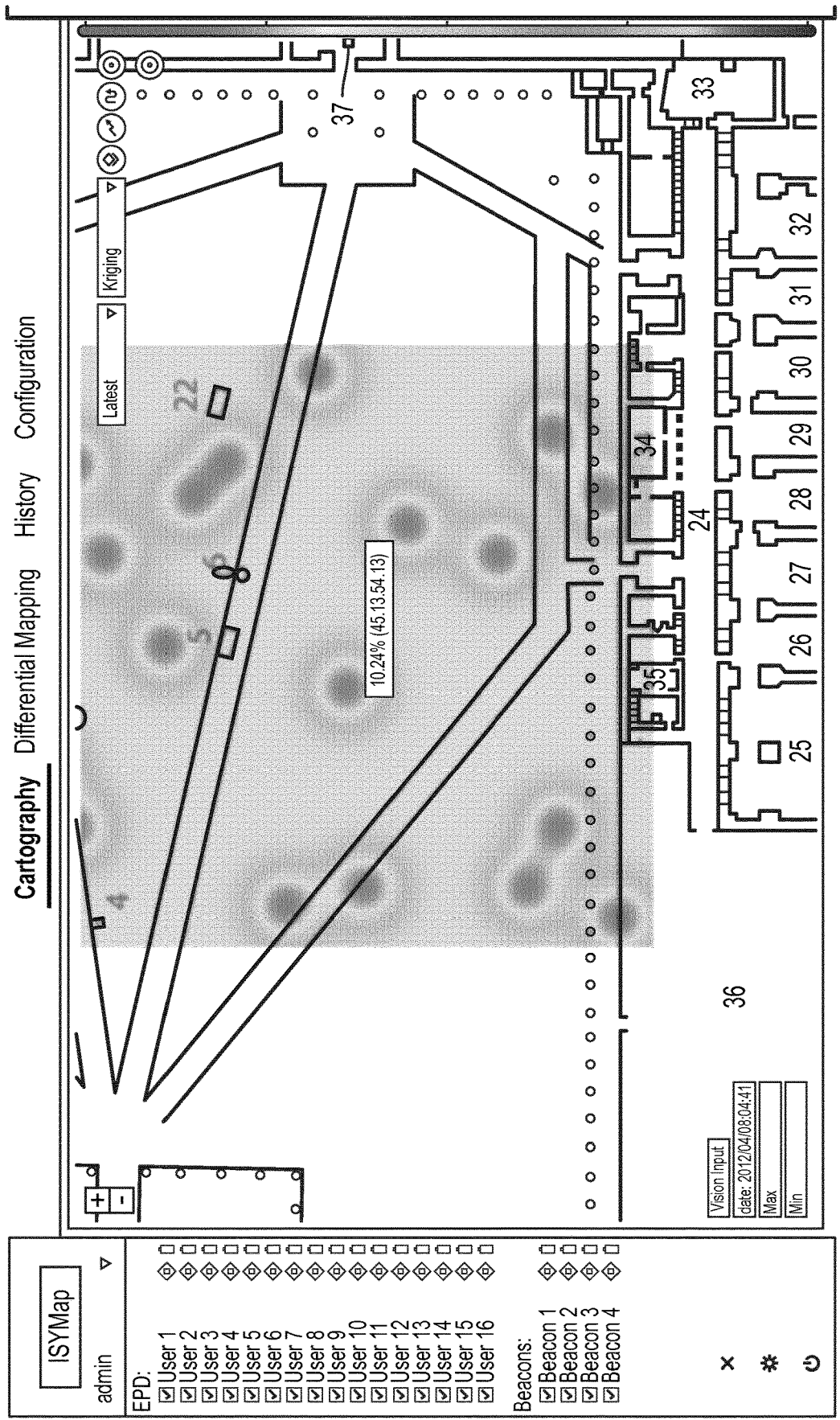
FIG. 10 shows an exemplary uncertainty map produced using the data acquired from a system in accordance with an embodiment of the present invention.

FIG. 10 is an uncertainty map of the data acquired from the portable devices and triangulation beacons in the environment shown in FIGS. 8 and 9. The variation in colour of the contour map reflects the uncertainty in, e.g., the determined dose rate at any given point. This map may be used to determine where within the environment it may be beneficial to receive additional dose rate measurements from in order to form a more accurate representation of the variation in dose rate throughout the environment.

Figure 11:
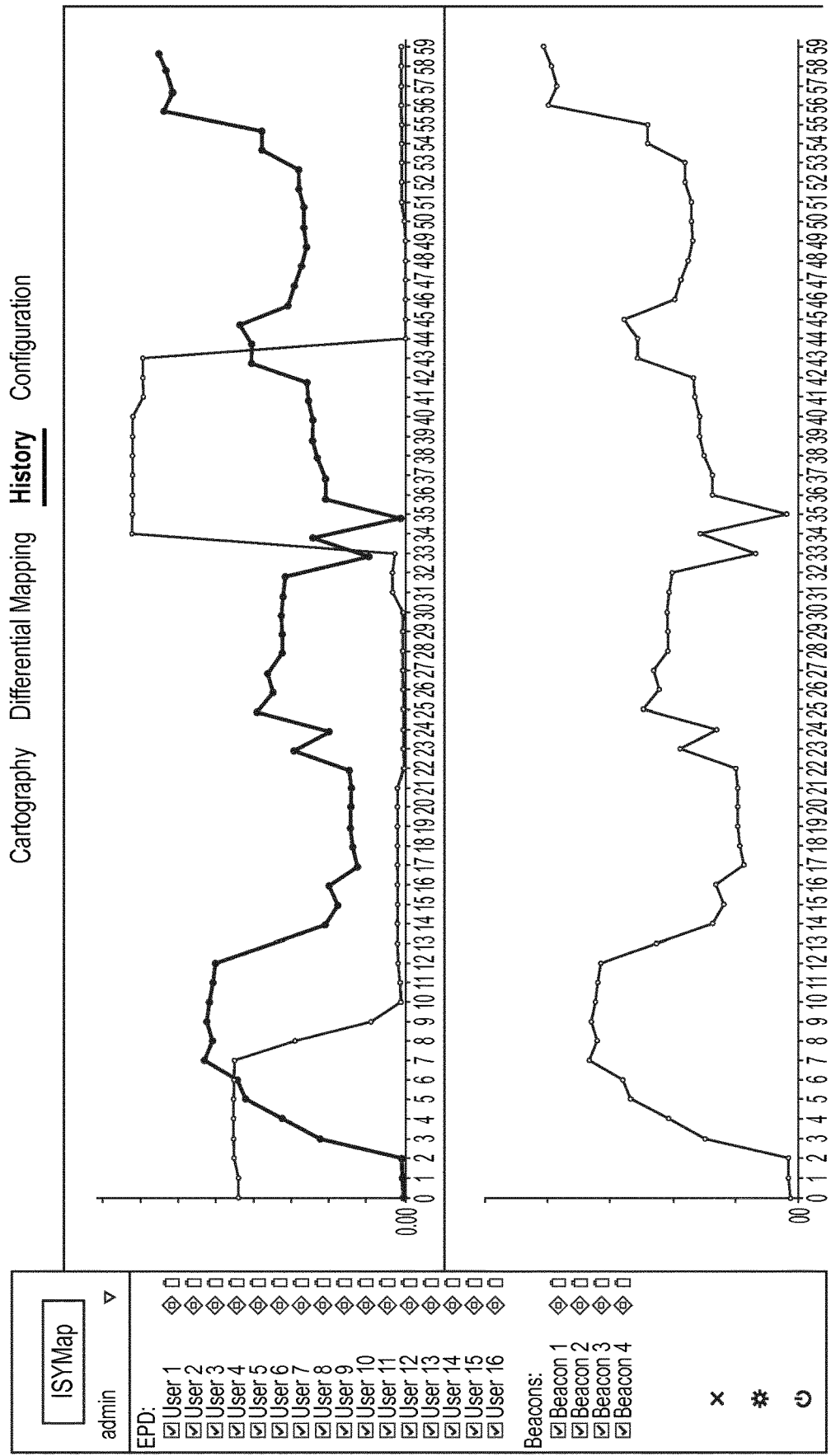
FIG. 11 is a graph of the measured dose rate against time using the data acquired from a system in accordance with an embodiment of the present invention.

FIG. 11 shows a graph of the dose rate of one or more selected portable devices and/or triangulation beacons over time, e.g. as collected in the environment shown in FIGS. 8-10. This graph shows the evolution, e.g. of dose rate, for a certain portable device and/or triangulation beacon over time.

The invention claimed is:

1. A system for monitoring the exposure of a plurality of individuals to a physical or chemical property associated with an environment, the system comprising:

a plurality of portable devices, wherein each portable device of the plurality of portable devices is arranged to be worn or carried by an individual in the environment;

a plurality of triangulation beacons positioned in fixed locations around the environment, wherein each triangulation beacon of the plurality of triangulation beacons is arranged to transmit a wireless signal to the plurality of portable devices in the environment, and wherein at least one triangulation beacon of the plurality of triangulation beacons comprises at least one radiation monitor arranged to measure radioactive materials to which the individual is exposed in the environment; and a control unit for communicating with each portable device of the plurality of portable devices;

wherein each portable device comprises:

a detector arranged to measure a physical or chemical property that the individual wearing or carrying the portable device is exposed to in the environment;

one or more physiological sensors each arranged to measure a physiological parameter of the individual;

a geolocation module comprising a receiver arranged to receive the wireless signals transmitted by the plurality of triangulation beacons, wherein the geolocation module is arranged to use the received wireless signals to determine a location of the individual; and a communication module for communicating data collected by the portable device with one or more portable devices of the plurality of the portable devices and with the control unit.

2. The system as claimed in claim 1, wherein the detector is arranged to capture data representative of the measurement of the physical or chemical property that the detector has measured.

3. The system as claimed in claim 1, wherein the detector comprises a further radiation monitor arranged to measure radioactive materials to which the individual is exposed in the environment.

4. The system as claimed in claim 1, wherein the one or more physiological sensors comprise one or more of: a temperature sensor arranged to measure the temperature of the individual, a heart rate monitor arranged to measure the heart rate of the individual, and a step counter arranged to measure the number of steps the individual takes.

5. The system as claimed in claim 1, wherein the geolocation module comprises a Global Navigation Satellite System receiver.

6. The system as claimed in claim 1, wherein one or more triangulation beacons of the plurality of triangulation beacons comprise one or more pseudolites.

7. The system as claimed in claim 1, wherein the respective locations of the portable devices are determined relative to the triangulation beacons.

8. The system as claimed in claim 1, wherein the system further comprises one or more communication units for communicating data collected by the portable devices with other(s) of the portable devices, with other(s) of the communication unit(s) and/or with the control unit, wherein the one or more communication units are positioned in respective fixed locations around the environment.

9. The system as claimed in claim 8, wherein one or more of the triangulation beacon(s) comprise one of the one or more communication units.

10. The system as claimed in claim 8, wherein at least one of the one or more communication units comprises at least one further detector arranged to measure a chemical and/or a physical property associated with the environment.

11. The system as claimed in claim 8, wherein the communication unit(s) are arranged to communicate the data collected by the triangulation beacon(s) and/or the communication unit(s) between the communication unit(s) and the portable devices, and/or back to the control unit.

12. The system as claimed in claim 8, wherein the data collected by the portable devices, the triangulation beacon(s) and/or the communication unit(s) is communicated by the triangulation beacon(s) and/or by the communication unit(s) to the control unit by a wired or wireless connection.

13. The system as claimed in claim 1, wherein each portable device comprises a data storage module in data communication with the detector, the one or more physiological sensors and the geolocation module, wherein the data storage module is arranged to store data received from the detector, the one or more physiological sensors, and the geolocation module.

14. The system as claimed in claim 13, wherein each portable device is arranged to store the captured data in the data storage module when it is determined that the communication module of the portable device is not in communication with any of the other communication modules and the control unit.

15. The system as claimed in claim 1, wherein each portable device comprises a feedback module arranged to provide feedback to the individual wearing or carrying the portable device.

16. The system as claimed in claim 1, wherein the control unit is arranged to generate an output from the data collected by the plurality of portable devices.

17. The system as claimed in claim 1, wherein the control unit is arranged to use the captured and received data to generate maps and/or visualisations of the captured data and its respective locations in the environment.

18. A method of monitoring the exposure of a plurality of individuals to a physical or chemical property associated with an environment using a plurality of portable devices, the method comprising:

a plurality of individuals each wearing or carrying a portable device in an environment;

a detector of each portable device measuring a physical or chemical property that the individual wearing or carrying the portable device is exposed to in the environment;

one or more physiological sensors of each portable device each measuring a physiological parameter of the individual;

a geolocation module of each portable device determining the location of the individual;

wherein each portable device comprises a data storage module, in data communication with the detector, the one or more physiological sensors, and the geolocation module;

wherein the data storage module is arranged to store data received from the detector, the one or more physiological sensors and the geolocation module;

communicating data collected by the plurality of portable devices between portable devices and to a control unit;

determining if a communication module of the portable device is in communication with communication modules of any of the other portable devices and the control unit; and upon determining that the communication module of the portable device is not in communication with any of the other communication modules and the control unit, storing the captured data in the data storage module.

19. A system for monitoring the exposure of a plurality of individuals to a physical or chemical property associated with an environment, the system comprising:
  a plurality of portable devices, wherein each portable device of the plurality of portable devices is arranged to be worn or carried by an individual in the environment; and
  a control unit for communicating with each portable device of the plurality of portable devices;
  wherein each portable device comprises:
    a detector arranged to measure a physical or chemical property that the individual wearing or carrying the portable device is exposed to in the environment;
    one or more physiological sensors each arranged to measure a physiological parameter of the individual;
    a geolocation module arranged to determine a location of the individual;
    a communication module for communicating data collected by the portable device with one or more other portable devices of the plurality of the portable devices and with the control unit; and
    a data storage module in data communication with the detector, the one or more physiological sensors and the geolocation module;
  wherein the data storage module is arranged to store data received from the detector, the one or more physiological sensors and the geolocation module;
  wherein the system is arranged to determine if the communication module of the portable device is in communication with any of the other communication modules and the control unit; and
  wherein each portable device is arranged to store the captured data in the data storage module upon determining that the communication module of the portable device is not in communication with any of the other communication modules and the control unit.

* * * * *